United States Patent [19]
Correia

[11] Patent Number: 5,865,812
[45] Date of Patent: Feb. 2, 1999

[54] FLUID FLOW CONTROL APPARATUS FOR SURGICAL CANNULAE

[75] Inventor: James Correia, Shelton, Conn.

[73] Assignee: United States Surgical Corporation, Norwalk, Conn.

[21] Appl. No.: 820,069

[22] Filed: Mar. 19, 1997

Related U.S. Application Data

[63] Continuation of Ser. No. 534,610, Sep. 27, 1995, abandoned.

[51] Int. Cl.[6] .................................................. A61M 5/00
[52] U.S. Cl. ........................... 604/248; 604/167; 604/169
[58] Field of Search ................................. 604/248, 30, 32, 604/27, 158, 161, 162, 164, 167, 169, 171, 33, 249, 284; 251/352, 304, 298, 208, 210

[56] References Cited

U.S. PATENT DOCUMENTS

| | | |
|---|---|---|
| 2,261,213 | 11/1941 | Bierman . |
| 2,646,042 | 7/1953 | Quang . |
| 2,854,027 | 9/1958 | Kaiser et al. . |
| 3,185,179 | 5/1965 | Harautuneian . |
| 3,344,785 | 10/1967 | Hamilton . |
| 3,678,959 | 7/1972 | Liposky ................................. 604/33 X |
| 3,678,960 | 7/1972 | Leibinsohn . |
| 3,783,900 | 1/1974 | Waldbillig . |
| 3,834,372 | 9/1974 | Turney . |
| 3,952,729 | 4/1976 | Libman et al. . |
| 4,219,021 | 8/1980 | Fink . |
| 4,535,773 | 8/1985 | Yoon . |
| 4,601,710 | 7/1986 | Moll . |
| 4,738,265 | 4/1988 | Ritchart et al. . |
| 4,943,280 | 7/1990 | Lander . |
| 4,967,797 | 11/1990 | Manska . |
| 5,074,334 | 12/1991 | Onodera ................................. 604/32 X |
| 5,097,842 | 3/1992 | Bonn ....................................... 604/33 X |
| 5,116,353 | 5/1992 | Green . |
| 5,226,876 | 7/1993 | Filipi et al. . |
| 5,256,147 | 10/1993 | Vidal et al. . |
| 5,256,149 | 10/1993 | Banik et al. . |
| 5,334,163 | 8/1994 | Sinnett . |
| 5,347,992 | 9/1994 | Pearlman et al. . |
| 5,350,362 | 9/1994 | Stouder, Jr. ............................. 604/167 |
| 5,356,421 | 10/1994 | Castro ................................. 604/164 X |
| 5,376,071 | 12/1994 | Henderson . |
| 5,439,452 | 8/1995 | McCarty . |
| 5,578,016 | 11/1996 | Zinger ..................................... 604/248 |
| 5,655,541 | 8/1997 | Vattuone ................................. 120/749 |

FOREIGN PATENT DOCUMENTS

| | | |
|---|---|---|
| 2005807 | 10/1978 | United Kingdom . |
| WO 93/09722 | 5/1993 | WIPO . |

Primary Examiner—Ronald Stright, Jr.
Assistant Examiner—N. Kent Gring

[57] ABSTRACT

A surgical cannula assembly is provided having a housing defining a channel extending from a proximal end to a distal end of the housing, at least one fluid flow regulator member disposed across the channel, which forms a substantial barrier to the passage of fluids in at least one direction, a cannula extending from the housing distal end in fluid communication with the channel, and a selector valve operatively connected to the cannula assembly housing and movable to at least a first orientation establishing a first fluid pathway from the channel to the environment outside the housing and a second orientation establishing a second fluid pathway from the channel to the outside environment.

11 Claims, 7 Drawing Sheets

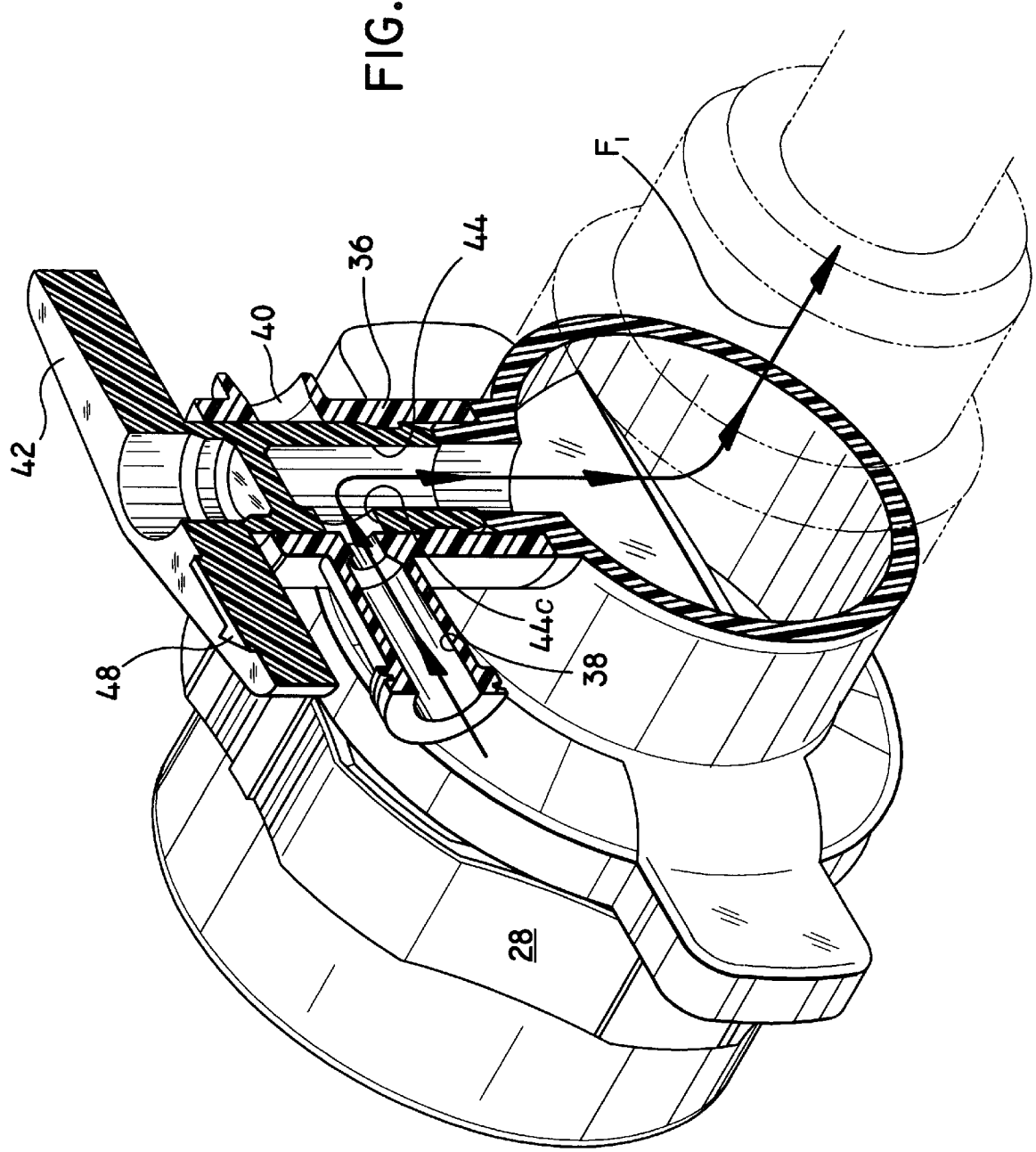

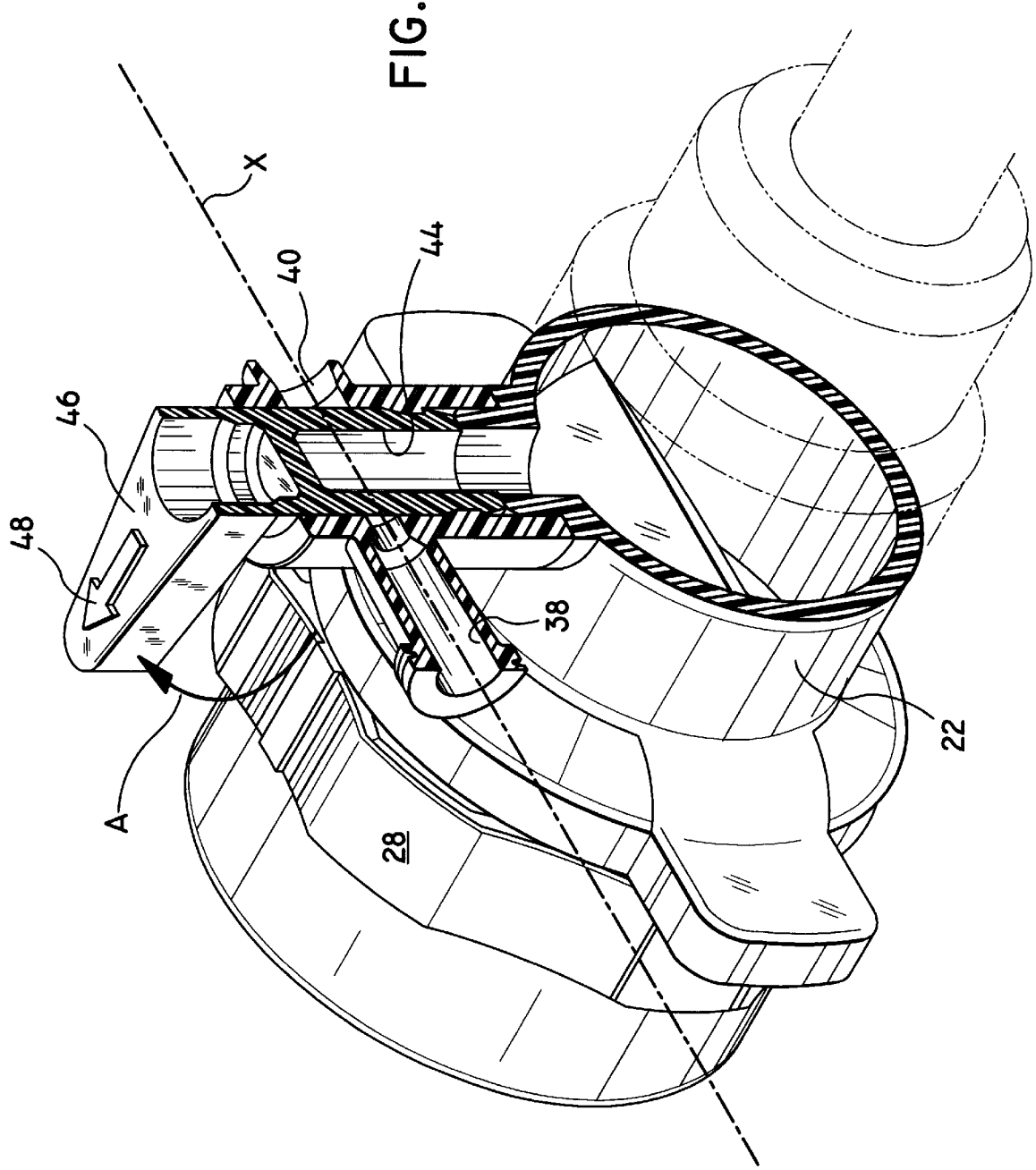

this is a continuation of application Ser. No. 08/534,610 filed on Sep. 27, 1995, now abandoned.

FLUID FLOW CONTROL APPARATUS FOR SURGICAL CANNULAE

This is a continuation of application Ser. No. 08/534,610 filed on Sep. 27, 1995, now abandoned.

BACKGROUND

1. Technical Field

The present disclosure relates to surgical cannula assemblies and more particularly, to fluid flow control selector apparatus for surgical cannulae.

2. Description of Related Art

Insufflatory surgery involves filling a body cavity with a pressurized gas, normally $CO_2$, to maintain the cavity under a certain predetermined pressure. One way of performing the surgery is by first puncturing the skin in a desired body cavity region with a needle. The needle, typically a Verres needle, includes a stylet which introduces an insufflation gas into the body cavity to inflate it.

A trocar is then used to puncture the body cavity. The trocar is inserted through a cannula or sheath, which cannula partially enters the body cavity through the incision made by the trocar. The trocar may then be removed from the cannula, and a surgical instrument such as an endoscope, graspers, clip appliers, forceps, etc., may be inserted through the cannula to perform the desired task within the anatomical cavity.

Various types of cannula or trocar assemblies are provided with valves for maintaining a certain gas pressure in the cavity when the trocar or other surgical instrument is removed from the cannula. One example of such an assembly is disclosed in U.S. Pat. No. 4,943,280 to Lander which features a cannula assembly having a flapper valve that is biased toward a closed position when no surgical instrument is inserted in the cannula assembly. In such devices, in order to rapidly desufflate the body cavity, the flapper valve may be selectively biased to the open position by a lever provided on the exterior of the cannula housing.

Another type of cannula or trocar assembly that maintains the seal of the insufflated body cavity utilizes one-way valve members, for example, elastomeric duck bill valves, to effectively retain the insufflation gases. Such devices have a stop-cock valve with a single fluid passageway located distal of the duck bill valve to facilitate the insufflation or desufflation of fluids from the body cavity. However, in order to desufflate, the insufflatory tubing must generally be removed therefrom.

One disadvantage of such cannula assemblies is that the maximum rate of insufflation and desufflation are equal due to the diameter of the single fluid passageway formed by the stop-cock with the channel of the cannula housing. Such devices, do not provide the user with the ability to selectively open the duck-bill in a similar manner as for the flapper valve, disclosed in U.S. Pat. No. 4,943,280 to Lander. Therefore, a need exists to provide a surgical cannula or trocar assembly which provides the user with a stop-cock assembly having a plurality of fluid flow paths to provide the ability to selectively insufflate or desufflate the body cavity without the necessity of adjusting or repositioning insufflatory tubing or the like.

SUMMARY

The present disclosure provides a surgical cannula assembly, which includes a housing defining a channel extending from a proximal end to a distal end of the housing, at least one fluid flow regulator member disposed across the channel, which forms a substantial barrier to the passage of fluids in at least one direction, a cannula extending from the housing distal end in fluid communication with the channel, and a selector valve operatively connected to the cannula assembly housing and movable to at least a first orientation establishing a first fluid pathway from the channel to the environment outside the housing and a second orientation establishing a second fluid pathway from the channel to the outside environment.

The selector valve is preferably movable to a third orientation preventing fluid communication between the channel and the outside environment through the selector valve. In one embodiment, the selector valve includes a body portion and a flow control selector slidably disposed relative to the body portion. In a currently preferred embodiment, the flow control selector is rotatably disposed within the body portion. The flow control selector may be in the form of a plug portion having first and second bores formed therethrough which define the first and second fluid passageways. The flow control selector may further include a handle portion extending from the plug portion to facilitate orientation of the selector valve to either the first position or the second position.

In a preferred embodiment the fluid flow regulator member is a seal defining an aperture. A particular fluid flow regulator may be in the form of a duck-bill valve.

BRIEF DESCRIPTION OF THE DRAWINGS

Preferred embodiments of the presently disclosed surgical cannula are described hereinbelow with reference to the drawings, wherein:

FIG. 4 is a cross-sectional perspective view of the housing of the cannula assembly of FIG. 1;

FIG. 5 is a view similar to FIG. 4, which shows the selector valve positioned in a closed position;

DETAILED DESCRIPTION OF THE PREFERRED EMBODIMENTS

Figure 1:
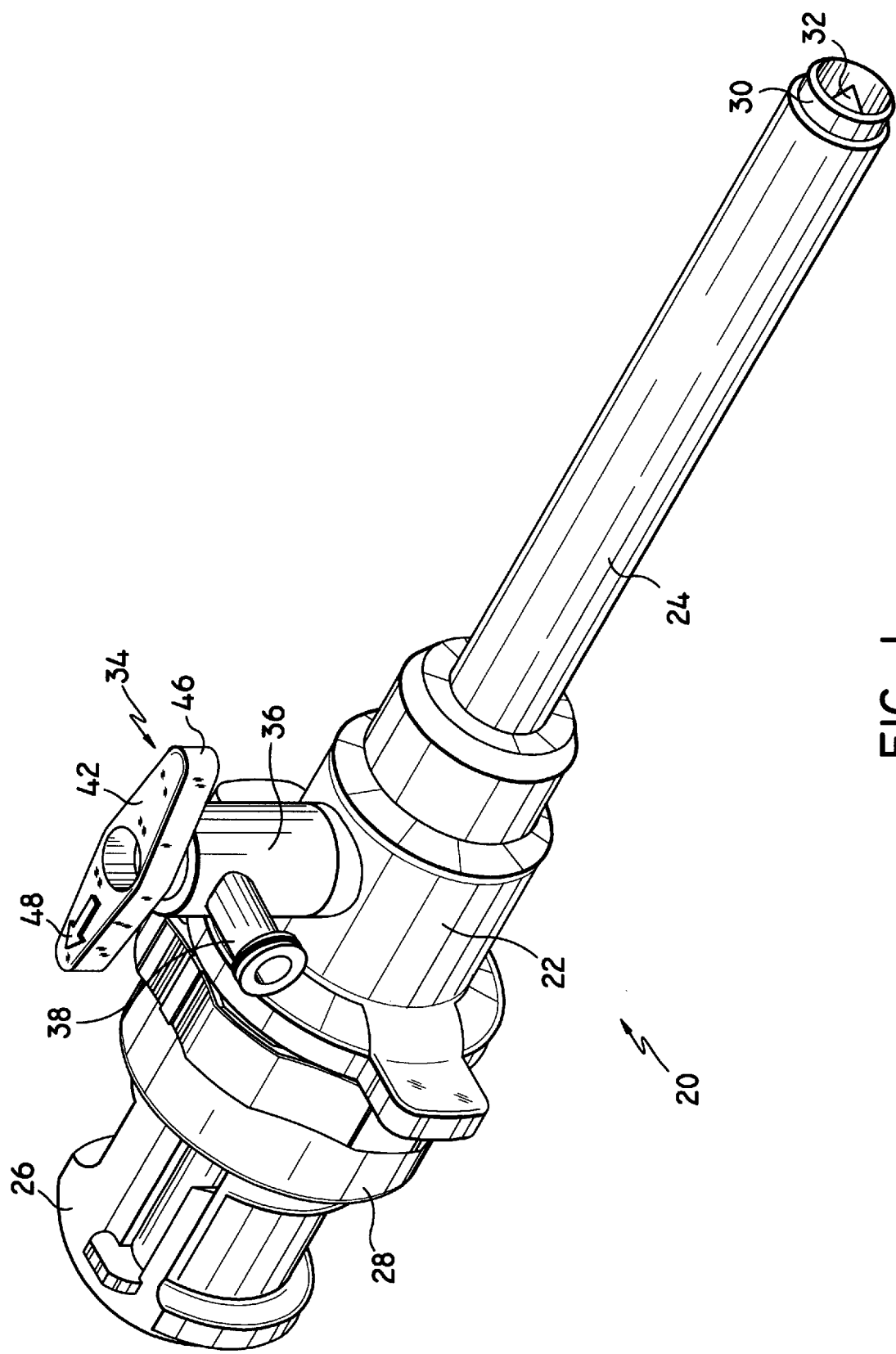
FIG. 1 is a perspective view of a currently preferred embodiment of the surgical cannula assembly.

With reference to the drawings, wherein like reference numerals identify similar or identical elements, and initially to FIGS. 1–2 and 4–6, a currently preferred embodiment of the surgical cannula assembly is shown as cannula assembly 20. While disclosed in detail consistent with applicant's duty to describe the "best mode" for practicing the claimed subject matter, the selector valve assembly depicted in FIGS. 1–2 and 4–6 includes contributions of individuals not included as inventors herein. The embodiment of FIGS. 7–10, however, reflects exclusively the inventive contributions of the presently named inventor. Insofar as the embodiment of FIGS. 1–2 and 4–6 falls within the scope of the claims appended hereto, such embodiment is deemed to fall within the scope of the present applicant's claimed invention.

Briefly, cannula assembly 20 includes a housing 22 which is preferably cylindrically shaped along inner wall 23, which defines a central longitudinal channel passing therethrough. An elongated cannula 24 extends from the distal end of housing 22 so as to form a continuous longitudinal fluid passageway with the channel defined by inner wall 23.

Except where noted otherwise, the materials utilized in the components of the presently disclosed embodiments generally include such materials as polycarbonate for housing sections and related components, and stainless steel, particularly for components which transmit forces. One preferred material is a polycarbonate material available from General Electric under the trade name LEXAN. Other specific preferred materials such as nylon or glass filled nylon (for strength) may also be utilized. However, equivalent alternative materials will readily come to the mind of those skilled in the art.

In FIG. 1, an obturator 26 is shown inserted through the proximal end of cannula assembly 20 and in particular passing through seal assembly adapter 28 which is threadably connected to cannula housing 22. Obturator 26 includes a cannula sheath 30 which extends out of the distal end of cannula 25 and which shields a trocar penetration tip 32.

In order to insufflate or desufflate a body cavity of a patient into which cannula 20 is inserted, a selector valve 34 is provided which is operatively secured to cannula housing 22 by body portion 36 being securely mounted to port 39 such as, for example, by bonding or other suitable attachment techniques. Selector valve 34 is provided with a first port such as inlet port 38 which facilitates the introduction of insufflation fluids, for example, $CO_2$ gas, into the body cavity, as will be described further herein.

Figure 2:
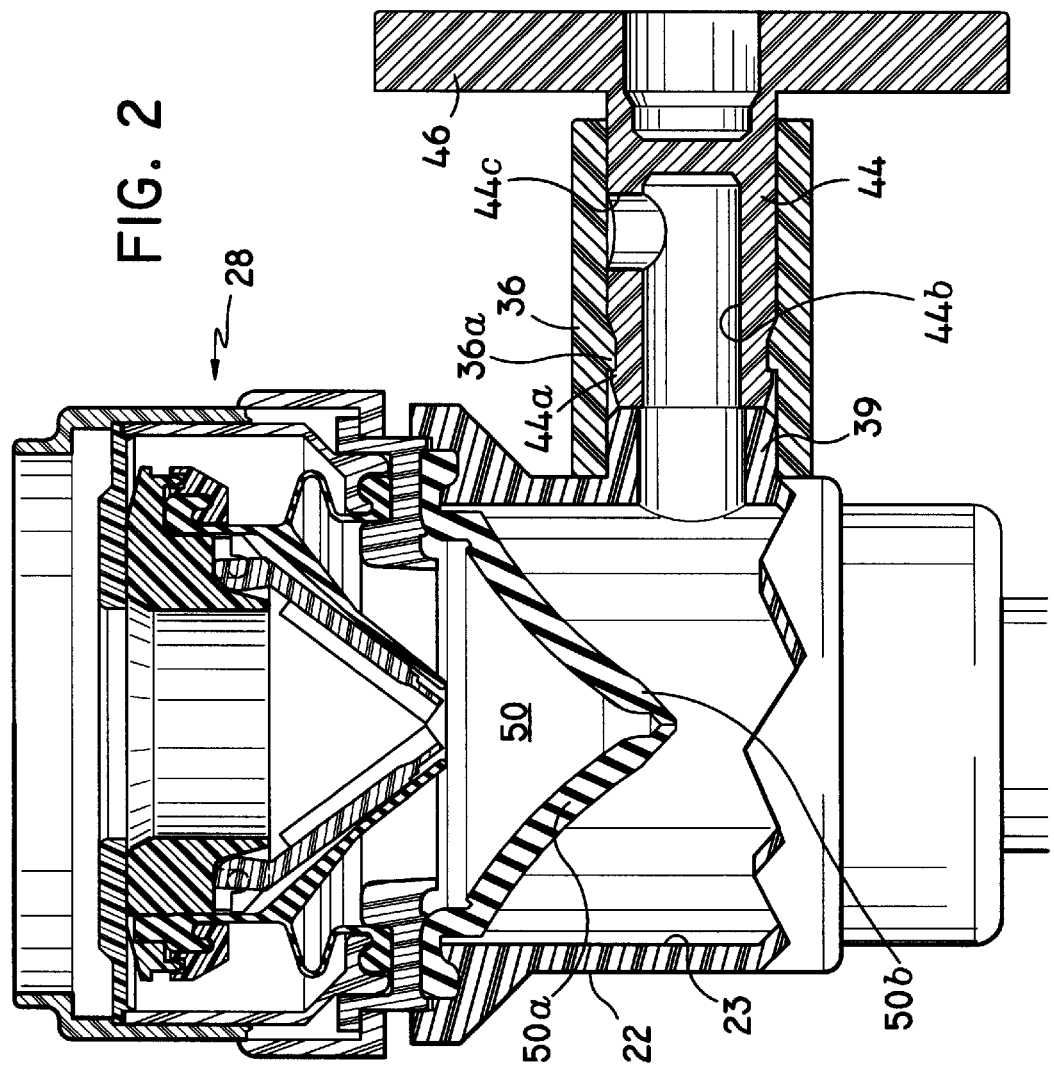
FIG. 2 is a partially cutaway view of the housing portion of the cannula assembly of FIG. 1.

A second port such as desufflation port 40 is provided through the wall of body portion 36 to enable the rapid desufflation of fluids from the body cavity, in particular the insufflation gases. A flow control selector 42 is inserted within the fluid passageway defined by body portion 36 of selector valve 34. As best illustrated in FIG. 2, flow control selector 42 is preferably secured within body portion 36, for example, by an annular collar 44a formed at the inwardly extending end of flow control selector 44 overlapping and interlocking with a shoulder portion 36a of body portion 36. Flow control selector 44 includes a fluid passageway which is defined by cylindrical inner wall portions 44b and 44c, the operation of which will be described further herein.

A handle 46 is provided on plug portion 44 and is preferably molded integrally therewith. Handle 46 provides the user with a mechanical advantage to facilitate rotation of plug portion 44 to orient the fluid passageway defined by inner wall portions 44b and 44c as desired. Inner wall portion 44c defines an outlet extending through the wall of plug portion 44. A flow indicator, such as raised arrow portion 48 is provided to give the user an indication as to the relative positioning of the outlet defined by inner wall 44c, as best illustrated in FIG. 4.

Figure 3:
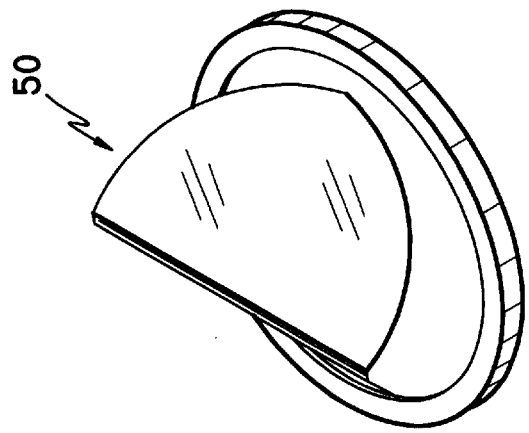
FIG. 3 is a perspective view of a duck bill valve which is incorporated into the presently disclosed cannula assembly.

Referring again to FIGS. 2 and 3, the various seal and valve components are illustrated therein. A fluid flow regulator, such as duck bill valve 50, formed of an elastomeric material is seated in an annular groove formed in cannula housing 22 and extends across the channel formed by inner wall portion 23. Duck bill 50 has a pair of flaps 50a and 50b which converge to form a one-way valve which prevents the escape of fluids from the insufflated body cavity. As shown in FIG. 2, the back pressure provided by the insufflation gases causes leaf flaps 50a and 50b to bow inwardly when no instrument is present in the channel, thereby forming a seal at their junction.

Seal adaptor 28, as noted above, is preferably threadably attached to cannula housing 22 and is removable to facilitate the withdrawal of items from within the body cavity such as, tissue samples or other matter removed from within the body cavity. Seal adaptor 28 is described in detail in copending, commonly assigned U.S. patent appln. Ser. No. 08/287,395 entitled Valve System for Cannula Assembly to Smith, the contents of which are hereby incorporated by reference.

The operation of selector valve 34 will now be described with reference to FIGS. 4–6. As set forth above, flow control selector 42 is rotatably mounted within body portion 36 of selector valve 34. When it is desired to introduce insufflation gases into the body cavity in which cannula assembly 20 is inserted, a source of gas (not shown), normally $CO_2$, is attached to first port 38 such as, for example, by a Luer lock connection. The insufflation gases travel along a fluid pathway illustrated by flow arrows "$F_1$", as shown in FIG. 4.

During the operative procedure, it is normally desirable to prevent the escape of insufflation gases through selector valve 34. To facilitate the containment of insufflation gases, flow control selector 42 is rotated in the direction of Arrow "A", as shown in FIG. 5 until the port defined by inner wall 44c of plug portion 44 is totally out of alignment with either first port 38 or second port 40. For example, such misalignment is illustrated in FIG. 5, wherein flow indicator 48 is substantially transversely oriented to an Axis "X", as defined by first port 38 and second port 40.

Figure 6:
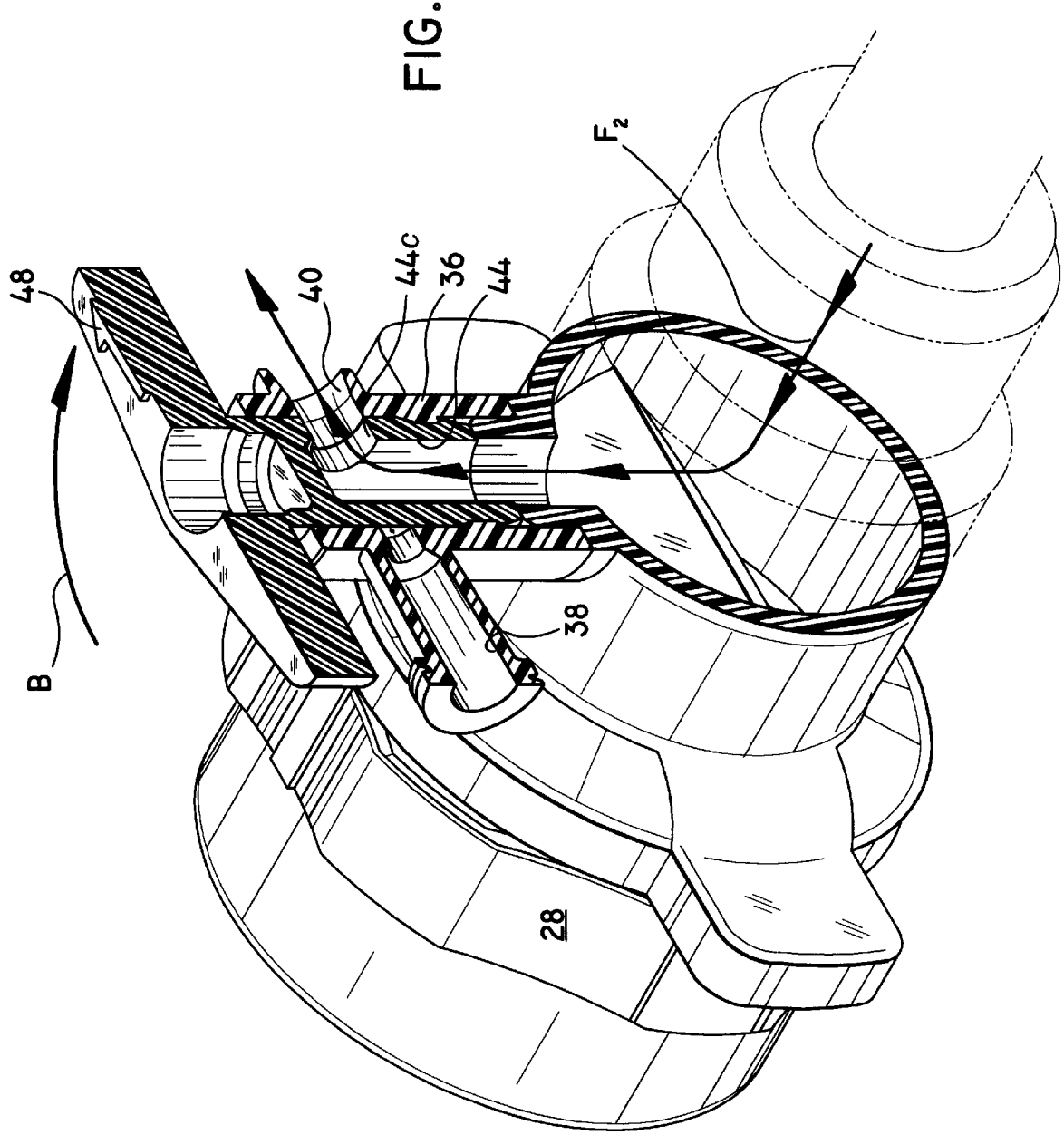
FIG. 6 is a view similar to FIGS. 4 and 5, which shows the selector valve positioned in one of two open positions.

Referring to FIG. 6, when it is desirable to permit the release of fluids, e.g., insufflation gases from the insufflated body cavity, flow control selector 42 is rotated in the direction of Arrow "B" until the port defined by inner wall 44c of plug portion is aligned with second port 40. The diameter of second port 40 is preferably substantially greater than the diameter of first port 38. This greater diameter of second port 40 facilitates the rapid desufflation of the gases contained within the body cavity. When flow control selector 42 is positioned as shown in FIG. 6, the insufflation gases travel along a fluid pathway illustrated by the fluid flow arrows designated "$F_2$".

Figure 7:
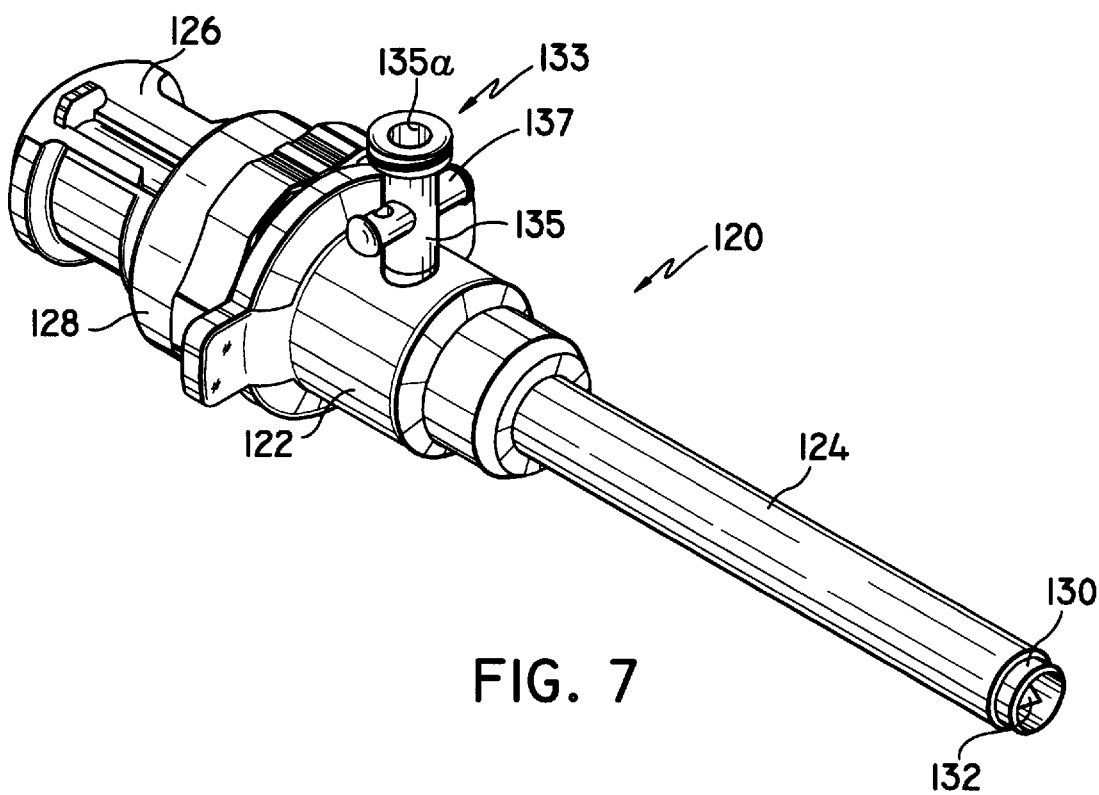
FIG. 7 is a perspective view of an embodiment of the cannula assembly of the present disclosure, as claimed herein.
Figure 8:
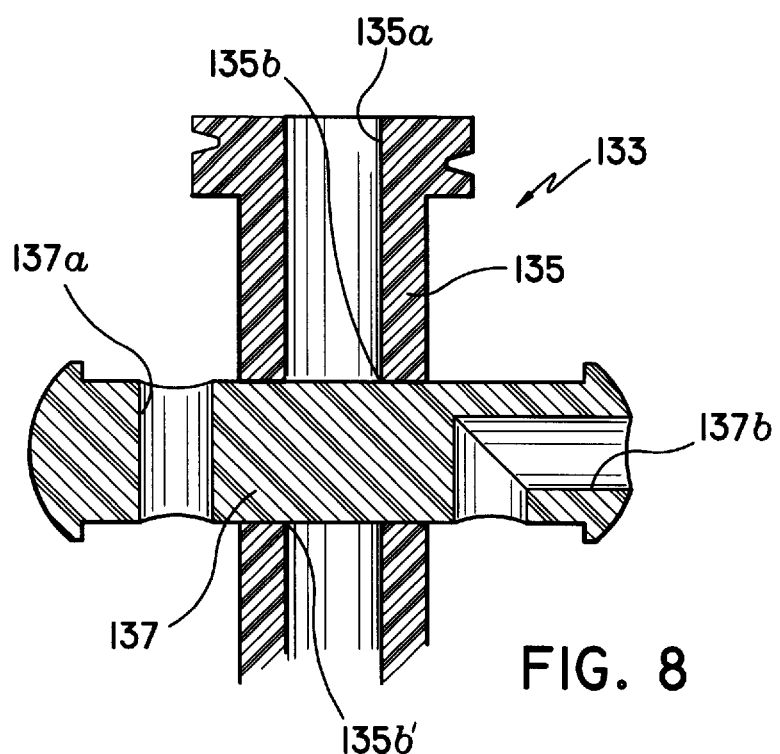
FIG. 8 is a cross-section view taken through the selector valve of the embodiment of FIG. 7.

An embodiment of cannula assembly 20, designated as cannula assembly 120 in FIGS. 7–10, will now be described. The components of cannula assembly 120 that are identical or similar to those of cannula assembly 20 are designated with reference numerals which correspond to those of cannula assembly 20, except that such designations are preceded by a "1". Accordingly, the following description will address in detail only the structural and operational differences between selector valve 34 and selector valve 133. Referring to FIGS. 7 and 8, selector valve 133 includes two main components, namely, body portion 135 and flow control selector 137 slidably disposed within a transverse bore formed through body portion 135.

Flow control selector 137 has an insufflation port defined by the inner wall 137a and a desufflation port defined by inner wall portion 137b. Body portion 135 defines a fluid passageway (or port) formed by inner wall 135a which passageway is in fluid communication with the channel defined by the inner wall of cannula housing 122, which is identical to that shown in FIG. 2, a second fluid passageway (or port) defined by opening 135b in an outer wall of body portion 135. A mirror image of the second fluid passageway is defined by an opening 135b' formed in the opposite outer wall of body portion 135. Together, openings 135b and 135b' accommodate motion of selector 137 relative to body portion 135. The relative dimensions of openings 135b, 135b' and the outer dimension of selector 137 are selected such that frictional engagement therebetween releasably maintains selector 137 in position relative to body portion 135 until repositioned by the user. Preferably, openings 135b, 135b' are circular and selector 137 has a substantially circular cross-section.

Figure 9:
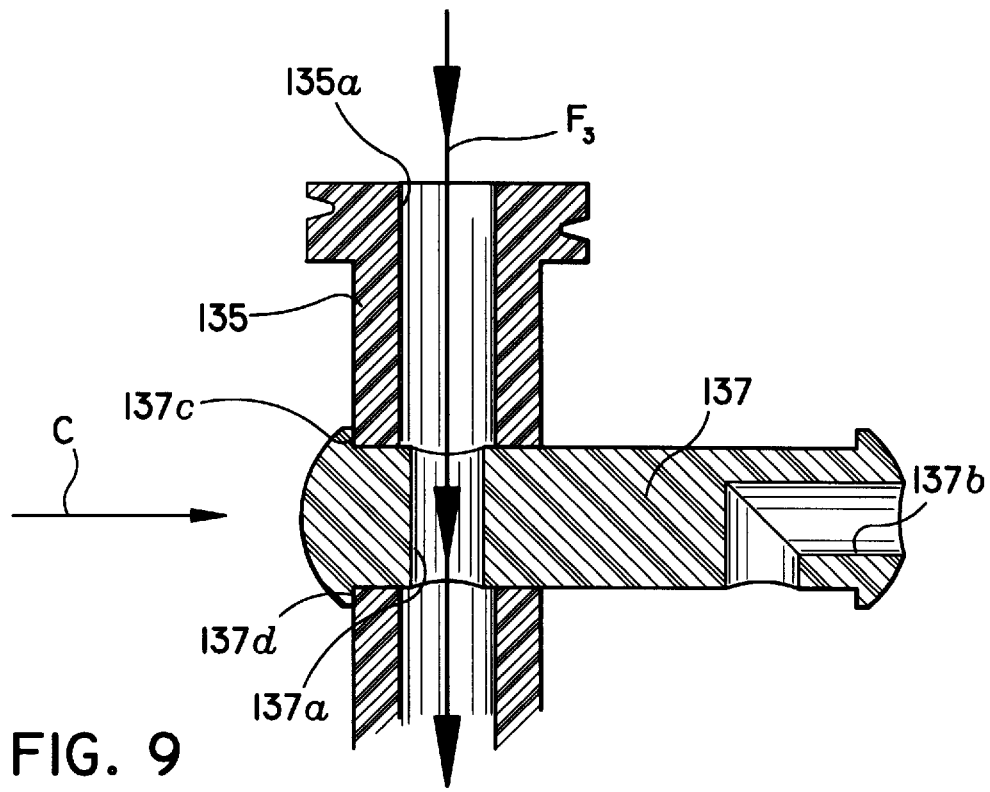
FIG. 9 is a view similar to FIG. 8, which shows the selector valve positioned in a first opened position.
Figure 10:
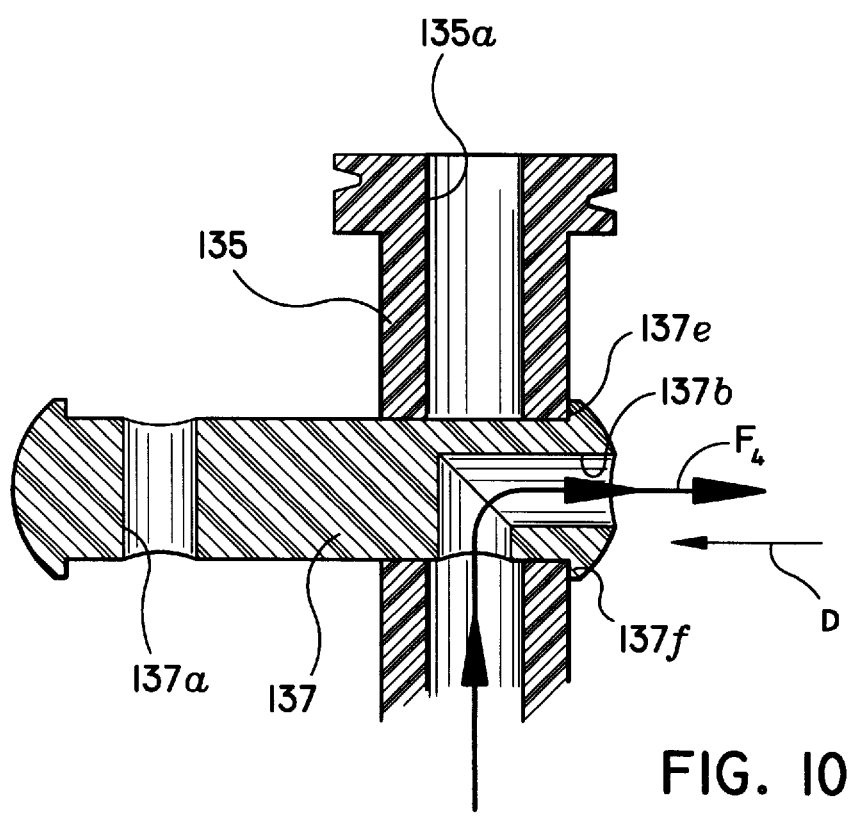
FIG. 10 is a view similar to FIGS. 8 and 9, which shows the selector valve positioned in a second open orientation.

In operation, as shown in FIGS. 9 and 10, flow control selector 133 permits the introduction of fluids, such as insufflation gases into the body cavity by urging flow control selector 137 in the transverse direction indicated by Arrow "C" in FIG. 9. Preferably, flow control selector is moved transversely until shoulder portions 137c and 137d abut against the outer wall of body portion 135 which indicates alignment of port 137a with the fluid passageway defined by inner wall 135a. Thereafter, insufflation gases may be introduced in the manner as described above, wherein the flow path of the insufflation gases is represented by the fluid flow arrows designated "F$_3$".

During the surgical procedure, when it is desirable to prevent the escape of fluids, such as insufflation gases from the body cavity, flow control selector 137 is moved transversely until flow control selector 137 is positioned as shown in FIG. 8, wherein the ends of flow control selector 137 extend substantially equidistantly from the openings formed on either side of body portion 135.

When it is desired to release fluids, such as the insufflation gases, i.e., desufflate the body cavity, flow control selector 137 is pushed transversely in the direction of Arrow "D", as indicated in FIG. 10, until shoulder portions 137e and 137f abut against the outer surface of body portion 136. This orientation provides indication to the user of the alignment of the fluid passageway defined by inner wall 135a and the fluid passageway defined by the inner wall 137b. Thus, a fluid flow path is established, which is indicated by the flow arrows designated "F$_4$".

What has been described is merely illustrative of the application of the principles of the present disclosure. Other arrangements and methods can be implemented by those skilled in the art without departing from the spirit and scope of the presently disclosed and claimed surgical cannula assembly embodiments.

What is claimed is:

1. A flow selector valve assembly for use with a cannula assembly housing having at least two openings, the flow selector including:
   (i) a body portion defining a fluid passageway in fluid communication with the housing, and a bore formed in fluid communication with the fluid passageway; and
   (ii) an elongated flow control selector slidable along an axis defined by the bore and including a first port extending substantially transversely through flow control selector and a second port having a first portion thereof defining an opening formed on a surface substantially parallel to the axis and extending partially through the elongated flow control selector in a first direction, and a second portion thereof defining an opening formed on a surface substantially perpendicular to the axis and extending partially through the elongated flow control selector in a second direction such that a continuous fluid path is formed which is not directly transverse through the elongated flow control selector;
   wherein the elongated flow control selector is positionable in at least a first orientation establishing a first fluid pathway from within the housing to the environment outside the housing and a second orientation establishing a second fluid pathway from within the housing to the outside environment.

2. A flow selector valve assembly according to claim 1, wherein the second port forms an outlet opening at one end of the elongated flow control selector.

3. A flow selector value assembly according to claim 1, wherein the elongated flow control selector is further positionable in a third orientation preventing fluid communication between the channel and the outside environment through the elongated flow control selector.

4. A flow selector valve assembly according to claim 1, wherein the second port is configured and dimensioned to redirect fluid flow orthogonally.

5. A flow selector valve assembly for use with a cannula assembly housing having at least two openings, the flow selector including:
   (i) a body portion defining a fluid passageway in fluid communication with the housing, and a bore formed in fluid communication with the fluid passageway; and
   (ii) an elongated flow control selector slidable along an axis defined by the bore and including a first port extending substantially transversely through flow control selector and a second port having a first portion thereof extending partially through the elongated, flow control selector in a first direction, and a second portion thereof extending partially through the elongated flow control selector in a second direction such that a continuous orthogonal fluid path is formed through the elongated flow control selector;
   wherein the elongated flow control selector is positionable in at least a first orientation establishing a first fluid pathway from within the housing to the environment outside the housing and a second orientation establishing a second fluid pathway from within the housing to the outside environment.

6. A flow selector valve assembly according to claim 5, wherein the second port forms an outlet opening at one end of the elongated flow control selector.

7. A flow selector value assembly according to claim 5, wherein the elongated flow control selector is further positionable in a third orientation preventing fluid communication between the channel and the outside environment through the elongated flow control selector.

8. A surgical cannula assembly, which comprises:
   a) a housing having a proximal end and a distal end, the housing defining a channel extending from the proximal end to the distal end of the housing, the housing further defining at least two openings in fluid communication with the channel;
   b) at least one fluid flow regulator member disposed across the channel, which forms a substantial barrier to the passage of fluids in at least one direction;
   c) a cannula extending from the housing distal end in fluid communication with the channel; and
   d) a flow selector valve assembly operatively connected to the cannula assembly housing in fluid communication with at least one of the at least two openings in the housing, the flow selector including:
      (i) a body portion defining a fluid passageway in fluid communication with the channel, and a bore formed in fluid communication with the fluid passageway; and (ii) an elongated flow control selector slidable along an axis defined by the bore and including a first port extending substantially transversely through flow control selector and a second port having a first portion thereof extending partially through the elongated flow control selector in a first direction, and a second portion thereof extending partially through the elongated flow control selector in a second direction such that a continuous fluid path is formed which is not directly transverse through the elongated flow control selector;

wherein the elongated flow control selector is positionable in at least a first orientation establishing a first fluid pathway from the channel to the environment outside the housing and a second orientation establishing a second fluid pathway from the channel to the outside environment.

9. A surgical cannula assembly assembly according to claim 8, wherein the second port is configured and dimensioned to redirect fluid flow orthogonally.

10. A surgical cannula assembly according to claim 9, wherein the second port forms an outlet opening at one end of the elongated flow control selector.

11. A surgical cannula assembly according to claim 8, wherein the elongated flow control selector is further positionable in a third orientation preventing fluid communication between the channel and the outside environment through the elongated flow control selector.

* * * * *